Oct. 25, 1949. W. E. STOKES Plant Pat. 887
JAPANESE HOLLY PLANT
Filed Nov. 8, 1947
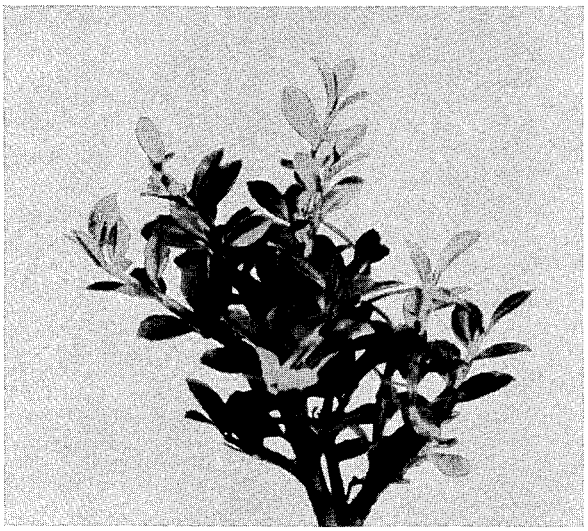
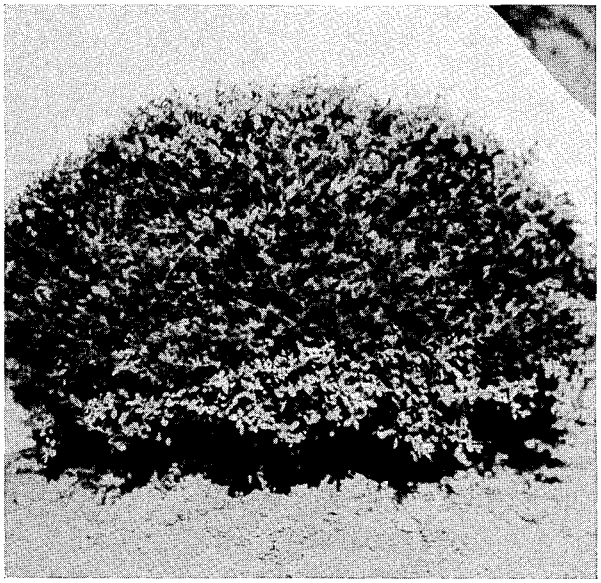
Warren E. Stokes
INVENTOR.
BY
Stebbins, Blenko & Webb
his attorneys Patented Oct. 25, 1949

Plant Pat. 887

UNITED STATES PATENT OFFICE

887

JAPANESE HOLLY PLANT

Warren E. Stokes, Butler, Pa.

Application November 8, 1947, Serial No. 784,879

1 Claim. (Cl. 47—59)

My invention relates to a new and distinct variety of Japanese holly plant or *Ilex crenata* plant which originated as a chance seedling. This new variety is endowed with a number of new and unusual characteristics which distinguish it from presently known varieties such as *Ilex convexa, Ilex Helleri, Ilex rotundifolia, Ilex microphilla* and *Ilex glabra.* Asexual reproduction of the new variety has shown that these new characteristics are permanently fixed through succeeding propagations.

My new variety of holly is very hardy, surpassing in this respect the majority of the varieties now known. However, the chief advantages of my holly are found in its habits of growth. It is exceedingly dwarf, compact and dense. It is somewhat flatly globular with dense foliage and compact branches such that the new growth completely obscures that of the previous season. The new foliage is a bright golden green completely free of the dull muddy tone of most *Ilex crenata* and as the season advances it turns to a soft shade of dark green which carries into the winter months.

The hardiness and habit of growth of my new variety of Ilex answer a long recognized want for a hardy dwarf evergreen suitable for an edging or border plant or as a dwarf hedge along walks or drives or at the top or base of stone walls. Moreover, it shears well and may be readily kept within a given design without damage to the plant.

My new variety of Ilex is not particular as to soil requirements, growing satisfactorily in moist or dry locations, in acid or alkaline soils, sand, clay or loam.

The prominent distinctions and characteristics of my new variety will be more clearly apparent by referring to the following detailed description and to the accompanying illustrations.

The drawing shows a branch with leaves, and a complete plant, of this variety.

Plant growth: The natural habit of growth is exceedingly dwarf and flatly globular. The plant is readily trained by shearing into a symmetrical rounded globe for use as a specimen plant. It holds its sheared form extremely well. The annual growth is short, often as little as one-half inch per year, except where ample rains fall well into the summer or under irrigation when a second growth may appear which may increase the total growth to one inch or more on mature plants, while on younger plants the growth may be longer, especially if well fertilized and watered. The new growth appears late in the spring (late May in the latitude of Pittsburgh), rendering it practically immune to late spring frost injury. It completely obscures the growth of the previous season.

Foliage:

*Color.*—Coloring of the foliage varies in the new growth and the old growth. The new growth is a bright golden green while the old growth is a soft shade of dark green.

*Form.*—The leaves are lanceolate in form, quite flat and very small—about $\frac{5}{16}$ inch long and about $\frac{1}{8}$ inch wide—with slight serrations. The leaves are very closely set, the space between nodes averaging about $\frac{1}{16}$ inch.

Hardiness: The variety is very hardy, surpassing in this respect *Ilex convexa, Ilex Helleri, Ilex rotundifolia, Ilex microphilla* and *Ilex glabra.*

I claim:

A new and distinct variety of Japanese holly plant, substantially as shown and described, characterized by its exceedingly dwarf, dense, compact habit of growth, the small size and closeness together of its leaves, its hardiness and its adaptability for either hedge or specimen use.

WARREN E. STOKES.

No references cited.